United States Patent [19]

Dhingra et al.

[11] Patent Number: 4,634,788

[45] Date of Patent: Jan. 6, 1987

[54] HERBICIDAL GLYPHOSATE OXIME DERIVATIVES

[75] Inventors: Om P. Dhingra, Creve Coeur; John E. Franz, Crestwood; Harrison R. Hakes, Ballwin, all of Mo.

[73] Assignee: Monsanto Company, St. Louis, Mo.

[21] Appl. No.: 741,930

[22] Filed: Jun. 6, 1985

[51] Int. Cl.$^4$ .............................................. C07F 9/40
[52] U.S. Cl. ..................................... 558/145; 558/170
[58] Field of Search ................. 558/170, 133, 173, 87, 558/145

[56] References Cited

U.S. PATENT DOCUMENTS

| | | | |
|---|---|---|---|
| 3,799,758 | 3/1974 | Franz | 71/86 |
| 3,970,695 | 7/1976 | Rueppel | 71/86 |
| 4,053,505 | 10/1977 | Dutra | 260/502.5 |
| 4,120,689 | 10/1978 | Dutra | 71/86 |

*Primary Examiner*—Anton H. Sutto
*Attorney, Agent, or Firm*—David Bennett; Arnold H. Cole

[57] ABSTRACT

Novel herbicidal oxime derivatives of aryl glyphosate esters are described and claimed along with a process for producing such oxime derivatives.

9 Claims, No Drawings

HERBICIDAL GLYPHOSATE OXIME DERIVATIVES

BACKGROUND TO THE INVENTION

The present invention relates to novel glyphosate oxime derivatives with herbicidal properties and to a process by which these derivatives may be obtained.

The discovery of the herbicidal properties of "glyphosate", the full chemical name of which is N-phosphonomethylglycine, has given rise to the discovery of a series of related derivatives with herbicidal properties. The basic patent in this area is U.S. Pat. No. 3,799,758 which discloses salts, esters and amides of glyphosate. Other patents including U.S. Pat. No. 4,053,505 and U.S. Pat. No. 4,120,689 have described the aryl esters and still others, such as U.S. Pat. No. 3,970,695, have claimed glyphosate derivatives with trifluoroacetyl substituents. There has however been no examination of the oxime ester derivatives of glyphosate since a a suitable process by which such compounds could be made has not previously been defined. The present invention provides such a process and the novel compounds made thereby have been found to exhibit herbicidal activity.

DESCRIPTION OF THE INVENTION

The novel compounds of the invention have the formula:

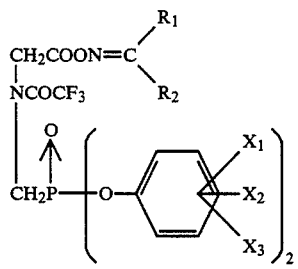

wherein $R_1$ and $R_2$ are each independently hydrogen alkyl, aryl, aralkyl or haloalkyl and $X_1$, $X_2$ and $X_3$ are each independently hydrogen, halogen, $C_1$–$C_4$ alkyl or alkoxy, or nitro groups.

In preferred compounds of the invention, $X_2$ and $X_3$ are hydrogen and $X_1$ is hydrogen, chloro or $C_1$ to $C_4$ alkyl. The preferred embodiments of $R_1$ and $R_2$ are hydrogen, phenyl and methyl with compounds in which at least one of $R_1$ and $R_2$ is methyl most preferred.

The invention further comprises a process for the preparation of the above compounds by the reaction of a compound having the structure:

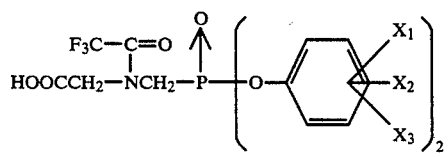

with an oxime having the structure

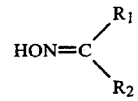

in an aprotic organic solvent and in the presence of a tertiary amine base and $N,N^1$-dicyclohexylcarbodiimide. In the above formula the terms $R_1$, $R_2$, $X_1$, $X_2$ and $X_3$ have the same significances as are set forth above.

The starting phosphonate ester in the above reaction can be obtained by the process described in U.S. Pat. No. 4,218,235. Alternatively it may be obtained by the procedures outlined in Example 1 with appropriate modifications.

The compounds of the invention are found to have post emergent herbicidal activity.

DESCRIPTION OF PREFERRED EMBODIMENTS

The following Examples illustrate preferred compounds according to the invention as well as preferred reactions by which they may be made. They are of course illustrative in nature and imply no limitations on the scope of the invention.

The process to produce the compounds of the invention takes place in any aprotic organic solvent capable of bringing the starting materials into solution. Usually dichloromethane, tetrahydrofuran or dimethyl formamide are suitable but others can also be used if desired if they remain inert to the reactants and starting materials.

The reaction between the oxime and the carboxylic acid function in the starting material is catalyzed by a tertiary amine such as 4-pyrrolidinopyridine, dimethylaminopyridine, triethylamine or pyridine. The preferred tertiary amine is however 4-pyrrolidinopyridine.

The reaction proceeds at room temperatures though elevated temperatures can be used if desired.

EXAMPLE 1

This Example illustrates the production of a compound according to the invention having the formula:

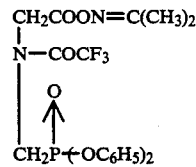

For purposes of illustration the production process starting from readily available materials is described. It is understood that this process could readily be adopted to produce other compounds according to the invention.

The initial reaction product (V) is produced in the following manner:

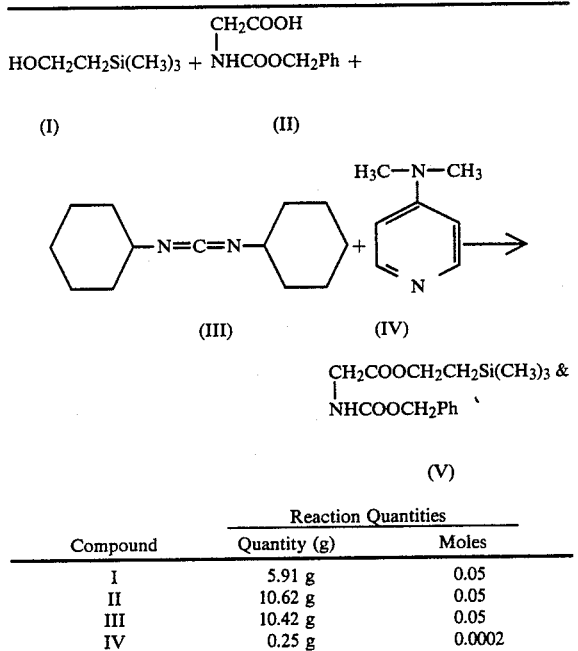

(I)   (II)   (III)   (IV)

CH₂COOCH₂CH₂Si(CH₃)₃ &
|
NHCOOCH₂Ph (V)

| Compound | Reaction Quantities | |
|---|---|---|
| | Quantity (g) | Moles |
| I | 5.91 g | 0.05 |
| II | 10.62 g | 0.05 |
| III | 10.42 g | 0.05 |
| IV | 0.25 g | 0.0002 |

Compounds I, II and IV were dissolved in 200 ml of 1,2-dichloroethane and the mixture was stirred magnetically under nitrogen. Compound III was then added and stirring at room temperature was continued overnight. After filtration, washing and finally concentration the reaction mixture yielded 15.5 g of Compound V.

Compound V (3.09 g or 10 mmol) was mixed with 20 ml of ethanol, 785 mg of acetyl chloride and 50 mg of 10% Pd/C catalyst. This mixture was stirred under hydrogen overnight. The catalyst was then filtered off through a Celite pad and the filtrate was concentrated to an oil which was further purified, concentrated and then dried to give 1.65 g of a product that proved to have the formula:

Cl⁻.H₃⁺NCH₂COOC₂H₄Si(CH₃)₃   (VI)

Compound VI (1.06 g or 5 mmole) was dissolved in 425 mg of tert-butylazomethine and 25 ml of diethyl ether. This mixture was stirred overnight at room temperature then filtered and the residue was washed with ether. The filtrate was concentrated to a colorless oil which crystallized to a white solid with a melting point of 42°–44° C. Elemental analysis which was consistent with structure VII below, showed: C—51.2%, H—9.15% and N—7.44%. The structure contains the theoretical proportions: C—51.3%, H—9.15% and N—7.48%.

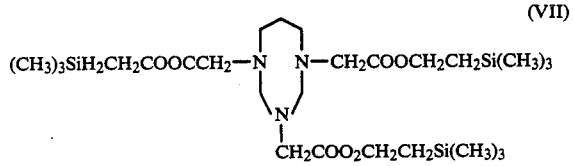

(VII)

Compound (VII) (27 mmol, 5.06 g) was mixed with 50 ml of toluene and 6.76 g (27 mmol+7%) of diphenylphosphite and the mixture was heated at 80° C. for 3 hours after which ³¹P NMR analysis indicated reaction was complete. The mixture was concentrated to leave a pale yellow oil which was dried under vacuum overnight. Elemental analysis showed the proportions C—57.2%, H—6.89% and N—3.10%. The expected structure (VIII below) contains: C—56.99%, H—6.7% and N—3.32%

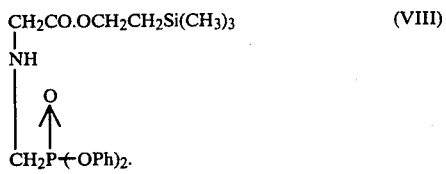

Compound (VIII) (7.0 g of the unpurified product) was dissolved in 15 ml of ethyl diisopropylamine and this solution was cooled to 0° C. A solution of 4.2 g of trifluoroacetic anhydride in 10 ml of diethyl ether was added dropwise with stirring which was continued overnight. After 16 hours a ³¹P NMR spectrum of the reaction mixture indicated a 40:60 ratio of starting materials to finished product. The mixture was then heated to 80° C. for 5 hours. The mixture was cooled to room temperature, diluted with ether, washed with 5% sulfuric acid, water and brine, and then dried over anhydrous sodium sulphate. Evaporation gave a yellow oil in which the major component was a compound with elemental analysis: C—51.05%, H—5.30% and N—2.64%. The expected compound, (IX below), has the theoretical proportions: C—51.06%; H—5.26% and N13 2.71%.

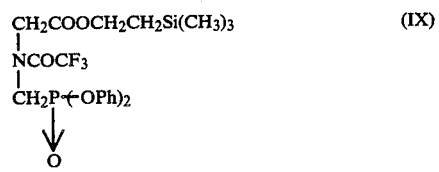

Compound (IX) (3.84 g) was stirred with 5 ml of trifluoroacetic acid for 3 hours. The mixture was then concentrated and dried under vacuum to yield a white solid. The solid was purified by reprecipitation from a 50/50 ether-cyclohexane mixture. The solid was dried overnight and an element analysis showed C—48.96%, H—3.65% and N—3.33%. Formula X below has the proportions C—48.93%, H—3.65% and N—3.30%.

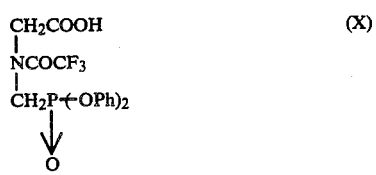

Compound X (834 mg or 2 mmol) was dissolved in 15 ml of dichloromethane and 454 mg (2.2 mmol) of Compound III were added. The mixture was stirred at room temperature. In a few minutes a precipitate of dicyclohexyl urea had formed. Acetone oxime (160.82 mg or 2.2 mmol) and 30 mg (0.2 mmol) of 4-pyrrolidinopyridine were then added and stirring at room temperature was continued overnight.

The mixture was diluted with diethyl ether and this solution was washed with water and brine and then dried. Evaporation of the solvent left a pale yellow oil. This product was purified by HPLC, using a 25% ethyl acetate/cyclohexane eluant. Fractions of 25 ml were collected at 25 ml/minute. The product appeared in fractions 17 to 30, and after evaporation 80 mg of a pale yellow oil were obtained.

NMR spectroscopy confirmed formation of the product:

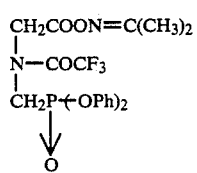

Elemental analysis yielded the following results: Theory: C 50.85%; H 4.27%; N 5–93% Found: C 50.79%; H 4.31%; N 5–96%.

EXAMPLE 2

This Example illustrates the production of a compound according to the invention having the formula:

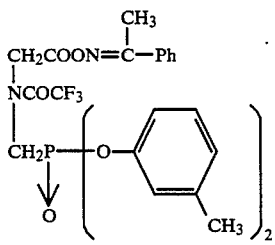

from a starting material with the formula:

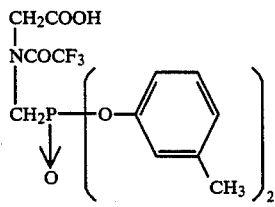

The above starting material (1.0 g or 0.0022 mole) was dissolved in about 5 ml of dichloromethane and 0.51 g (0.0024 mole) of N,N'dicyclohexylcarbodiimide dissolved in about 2 ml of dichloromethane was added with stirring, under nitrogen, at room temperature. A solid (dicyclohexyl urea) precipitated almost at once. Stirring was continued for 10 minutes. Phenyl methyl ketone oxime (0.33 g or 0.0024 mole) and 0.03 g (0.0002 mole) of 4-pyrrolidinopyridine were combined with 4 ml of dichloromethane and this clear yellow solution was added to the reaction mixture. After stirring overnight, more solvent was added to the mixture to replace evaporated solvent and agitation was continued. after three days the reaction mixture was filtered and then concentrated on a rotovap evaporator to a residue of 1.5 g. This was taken up in a small amount of dichloromethane and purified by an HPLC procedure. The eluant employed was 23% ethyl acetate/77% cyclohexane and the flow rate was 15 ml/minute.

The product obtained was shown to have structure VIII by proton and $^{31}P$ NMR spectroscopy.

Elemental analysis showed: Theory: C 57.65%; H 4.66%; N 4.98% Found: C 57.48%; H 4.93%; N 4.93%

EXAMPLE 3

This Example describes the production of a compound according to the invention having the formula:

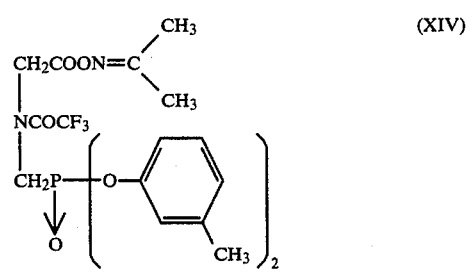

from a starting material having the formula:

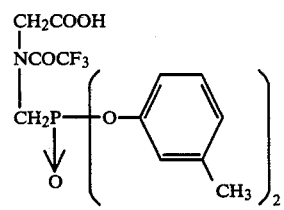

The starting material (2.0 g, 0.00449 mole) was dissolved in approximately 10 ml. of dichloromethane. To this mixture were added 1.02 g (0.00489 mole), of 99% N,N'dicyclohexylcarboiimide and about 4 ml. of dichloromethane. The mixture was stirred at room temperature under nitrogen. Almost immediately, dicyclohexylurea was precipitated. Stirring under nitrogen was continued for about 20 minutes.

Acetone oxime (0.36 g, 0.00492 mole) and 0.07 g (0.00047 mole) of 4-pyrrolidinopyridine were then mixed in about 3 ml. of dichloromethane and added to the reaction mixture which was stirred overnight at room temperature.

The reaction mixture was then filtered and the filtrate concentrated on a rotovap evaporator in a water bath at 25° C. The residue obtained (2.6 g) was purified by HPLC using a 500 ml. column, a flow rate of 500 ml/minute and a 40% ethyl acetate/60% cyclohexane eluant system.

The product obtained was subjected to elemental analysis and the following results were obtained:
C—52.71%; H—4.88%; N—5.59%
This is consistent with the formula of XIV (above) which has the theoretical proportions (based on the formula) of:

C—52.8%; H—4.83%; N—5.6%.
The Structure XIV was confirmed using proton $^{31}$P and $^{19}$F NMR spectroscopy.

EXAMPLE 4

TABLE 1

| Application Rate Kg/Ha | A | B | C | D | E | F | G | H | I | J | K | L | M | N | O | P | Q | R | S | T | Days After Treatment |
|---|---|---|---|---|---|---|---|---|---|---|---|---|---|---|---|---|---|---|---|---|---|
| Ex. 1 | | | | | | | | | | | | | | | | | | | | | |
| 11.2 | — | — | — | — | — | 2 | — | 2 | — | 1 | 1 | 1 | 0 | — | 2 | — | 1 | 0 | 0 | 2 | 11 |
| 11.2 | — | — | — | — | — | 2 | — | 2 | — | 2 | 3 | 2 | 2 | — | 3 | — | 1 | 0 | 2 | 2 | 34 |
| 5.6 | — | — | — | — | — | 2 | — | 2 | — | 3 | 1 | 1 | 0 | — | 2 | — | 1 | 0 | 0 | 2 | 11 |
| 5.6 | — | — | — | — | — | 2 | — | 2 | — | 3 | 3 | 1 | 0 | — | 3 | — | 2 | 0 | 2 | 2 | 34 |
| 5.6 | 2 | 3 | 3 | 3 | 3 | 3 | 3 | 2 | 4 | 4 | — | 3 | 3 | 4 | 4 | 4 | — | — | — | — | 15 |
| 1.12 | 0 | 1 | 0 | 0 | 0 | 0 | 0 | 0 | 0 | 1 | — | 0 | 0 | 1 | 1 | 2 | — | — | — | — | 15 |
| Ex. 2 | | | | | | | | | | | | | | | | | | | | | |
| 11.2 | — | — | — | — | — | 1 | — | 0 | — | 0 | 0 | 0 | 0 | — | 1 | — | 0 | 0 | 0 | 0 | 14 |
| 11.2 | — | — | — | — | — | 1 | — | 1 | — | 0 | 0 | 0 | 0 | — | 2 | — | 1 | 0 | 0 | 0 | 28 |
| 5.6 | — | — | — | — | — | 1 | — | 1 | — | 0 | 1 | 1 | 0 | — | 2 | — | 1 | 0 | 0 | 0 | 14 |
| 5.6 | — | — | — | — | — | 1 | — | 1 | — | 1 | 0 | 1 | 0 | — | 3 | — | 1 | 0 | 0 | 0 | 28 |
| 5.6 | 2 | 2 | 3 | 0 | 2 | 2 | 2 | 3 | 3 | 3 | 2 | 3 | 1 | 3 | 3 | 3 | — | — | — | — | 14 |
| 5.6 | 3 | 3 | 2 | 0 | 3 | 3 | 0 | 3 | 3 | 3 | 3 | 3 | 2 | 3 | 3 | 3 | — | — | — | — | 28 |
| 1.12 | 1 | 1 | 1 | 0 | 1 | 2 | 1 | 1 | 2 | 3 | 1 | 0 | 2 | 2 | 3 | 2 | — | — | — | — | 14 |
| 1.12 | 1 | 2 | 1 | 0 | 1 | 1 | 1 | 1 | 1 | 3 | 1 | 0 | 1 | 1 | 2 | 0 | — | — | — | — | 28 |
| .28 | 0 | 1 | 1 | 0 | 0 | 1 | 1 | 0 | 0 | 1 | 0 | 0 | 1 | 0 | 0 | 1 | — | — | — | — | 14 |
| .28 | 0 | 1 | 0 | 0 | 0 | 1 | 1 | 0 | 0 | 2 | 0 | 0 | 1 | 0 | 0 | 0 | — | — | — | — | 28 |

This Example illustrates the herbicidal activity of the compounds prepared by the process described in Examples 1 and 2.

The active ingredients are applied in spray form, at a rate equivalent to 200 gallons per acre, to 14 day old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (pounds per acre) of active ingredient. The treated plants are placed in a greenhouse and the effects are observed and recorded after approximately 2 weeks or approximately 4 weeks, as is indicated in the last column of Table I.

The post-emergence herbicidal activity index used in Table 1 is as follows:

| Plant Response | Index | Plant Response | Index |
|---|---|---|---|
| Less than 25% inhibition | 0 | 75–99% inhibition | 3 |
| 25 to less than 50% inhibition | 1 | 100% Inhibition | 4 |
| 50 to less than 75% inhibition | 2 | Not tested | — |

The plant species utilized in these tests are identified by letter in accordance with the following legend:

A — Soybean    K — Smartweed (Penn)
B — Sugar Beet    L — Velvetleaf
C — Wheat    M — Downy Brome
D — Rice    N — Proso Millet
E — Sorghum (grain)    O — Barnyardgrass
F — Cocklebur    P — Crabgrass (Large)
G — Wild Buckwheat    Q — Nutsedge (Yellow)*
H — Morningglory    R — Quackgrass*
I — Hemp Sesbania    S — Johnsongrass*
J — Lambsquarters (Common)    T — Canada thistle*

*Established from vegetative propagules.

The results obtained are set forth in Table 1.

What is claimed is:

1. A compound having the formula:

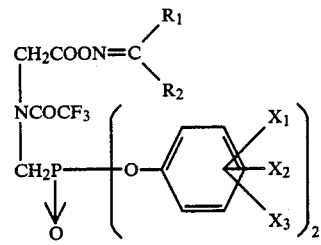

wherein $R_1$ is hydrogen or $R_2$ and $R_2$ is selected from alkyl, aryl, aralkyl and haloalkyl; and $X_1$ $X_2$ and $X_3$ are each independently hydrogen, halogen, nitro or $C_1$–$C_4$ alkyl or alkoxy groups.

2. A compound according to claim 1 and which $X_1$ is hydrogen, chloro or a $C_1$–$C_4$ alkyl group and $X_2$ and $X_3$ are both hydrogen.

3. A compound according to claim 2 in which $R_1$ is selected from $C_1$–$C_4$ alkyl and phenyl and $R_2$ is $C_1$–$C_4$ alkyl.

4. A compound according to claim 1 in which $R_1$ is the same as $R_2$.

5. A process for the production of the glyphosate oxime derivatives of claim 1 which comprises reacting a compound having the formula:

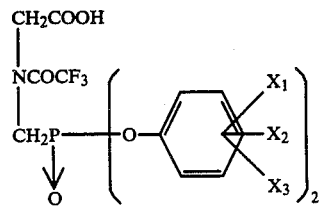

with an oxime having the formula $HON=C(R_1)(R_2)$ in an aprotic organic solvent and in the presence of a tertiary amine base and $N,N^1$-dicylcohexylcarbodiimide.

6. A process according to claim 5 in which $R_1$ is selected from $C_1$–$C_4$ alkyl and phenyl and $R_2$ is $C_1$–$C_4$ alkyl.

7. A process according to claim 5 in which $R_1$ is the same as $R_2$ and in which $X_2$ and $X_3$ are hydrogen.

8. A process according to claim 5 in which the reaction is conducted under an inert atmosphere.

9. A process according to claim 5 in which the base is 4-pyrrolidinopyridine.

* * * * *